(12) United States Patent
McKay et al.

(10) Patent No.: US 9,198,707 B2
(45) Date of Patent: Dec. 1, 2015

(54) NERVE AND SOFT TISSUE ABLATION DEVICE AND METHOD

(71) Applicant: Warsaw Orthopedic, Inc., Warsaw, IN (US)

(72) Inventors: William F. McKay, Memphis, TN (US); Josee Roy, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 328 days.

(21) Appl. No.: 13/835,424

(22) Filed: Mar. 15, 2013

(65) Prior Publication Data

US 2014/0276702 A1    Sep. 18, 2014

(51) Int. Cl.
*A61B 18/02* (2006.01)
*A61B 19/00* (2006.01)
*A61B 18/00* (2006.01)

(52) U.S. Cl.
CPC .............. *A61B 18/02* (2013.01); *A61B 19/5225* (2013.01); *A61B 19/5244* (2013.01); *A61B 2018/00577* (2013.01); *A61B 2018/0262* (2013.01); *A61B 2019/464* (2013.01)

(58) Field of Classification Search
CPC ........... A61B 18/02; A61B 2018/0231; A61B 2018/0262; A61B 2018/0268
USPC ...................................... 606/20–23
See application file for complete search history.

(56) References Cited

U.S. PATENT DOCUMENTS

| | | |
|---|---|---|
| 5,147,355 A | 9/1992 | Friedman et al. |
| 5,334,181 A | 8/1994 | Rubinsky et al. |
| 5,520,682 A | 5/1996 | Baust et al. |
| 5,906,612 A | 5/1999 | Chinn |
| 6,032,675 A | 3/2000 | Rubinsky |
| 6,179,831 B1 | 1/2001 | Bliweis |
| 6,190,378 B1 | 2/2001 | Jarvinen |
| 6,485,422 B1 | 11/2002 | Mikus et al. |
| 6,579,287 B2 | 6/2003 | Wittenberger et al. |
| 6,672,095 B1 | 1/2004 | Luo |
| 6,761,715 B2 | 7/2004 | Carroll |
| 6,789,545 B2 | 9/2004 | Littrup et al. |
| 6,796,979 B2 | 9/2004 | Lentz |
| 6,902,547 B2 | 6/2005 | Aves et al. |
| 6,926,711 B2 | 8/2005 | Lentz et al. |
| 7,166,075 B2 * | 1/2007 | Varghese et al. ............. 600/439 |
| 7,381,208 B2 | 6/2008 | Van Der Walt et al. |
| 7,510,554 B2 | 3/2009 | Duong et al. |
| 7,625,368 B2 | 12/2009 | Schechter et al. |

(Continued)

FOREIGN PATENT DOCUMENTS

WO    2010102310 A2    9/2010

*Primary Examiner* — Christopher D Koharski
*Assistant Examiner* — Michael Carey
(74) *Attorney, Agent, or Firm* — Sorell Lenna & Schmidt LLP

(57) ABSTRACT

An ablation device and method for monitoring and controlling temperature, pressure and position of an ablation probe for precise destruction of unwanted one of nerve tissue and soft tissue. The ablation device includes a probe configured to generate pressure and temperature for ablating the unwanted soft tissue and nerve tissue The device can also include a monitoring device, an imaging device, and a computer system. The probe includes at least two prongs, the at least two prongs each including distal ends, the distal ends being configured to define, in combination, a probe geometry substantially matching an anatomical tissue geometry of the unwanted one of nerve tissue and soft tissue.

25 Claims, 3 Drawing Sheets

(56) References Cited

U.S. PATENT DOCUMENTS

| | | |
|---|---|---|
| 7,641,679 B2 | 1/2010 | Joye et al. |
| 7,846,154 B2 | 12/2010 | Bliweis et al. |
| 7,938,822 B1 | 5/2011 | Berzak et al. |
| 7,967,814 B2 | 6/2011 | Levin |
| 7,967,815 B1 | 6/2011 | Berzak et al. |
| 8,083,733 B2 | 12/2011 | Toubia et al. |
| 8,162,812 B2 | 4/2012 | Shai et al. |
| 2002/0068964 A1 | 6/2002 | Dobak |
| 2004/0049177 A1 | 3/2004 | Zvuloni et al. |
| 2005/0177215 A1 | 8/2005 | Rosenberg |
| 2005/0240239 A1 | 10/2005 | Boveja et al. |
| 2006/0264920 A1* | 11/2006 | Duong ............... 606/21 |
| 2007/0156125 A1 | 7/2007 | DeLonzor |
| 2007/0191732 A1 | 8/2007 | Voegele |
| 2008/0306475 A1 | 12/2008 | Lentz et al. |
| 2009/0036823 A1 | 2/2009 | LePivert |
| 2009/0192505 A1 | 7/2009 | Askew et al. |
| 2009/0299357 A1 | 12/2009 | Zhou |
| 2010/0168739 A1 | 7/2010 | Wu et al. |
| 2010/0179527 A1 | 7/2010 | Watson et al. |
| 2010/0292764 A1 | 11/2010 | Soomro et al. |
| 2011/0160585 A1* | 6/2011 | Akyuz et al. ............... 600/443 |
| 2011/0270238 A1 | 11/2011 | Rizq et al. |
| 2011/0313411 A1 | 12/2011 | Anderson et al. |
| 2012/0046531 A1 | 2/2012 | Hua |
| 2012/0065630 A1 | 3/2012 | Berzak et al. |
| 2012/0089047 A1 | 4/2012 | Ryba et al. |
| 2012/0109116 A1* | 5/2012 | Asconeguy et al. ........... 606/21 |
| 2012/0253336 A1 | 10/2012 | Littrup et al. |

* cited by examiner

NERVE AND SOFT TISSUE ABLATION DEVICE AND METHOD

FIELD

The present invention relates generally to devices and methods for ablating a material or substance. More specifically, the devices and methods are useful for removing nerve and/or soft tissue to alleviate pain.

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

One alternative approach that is commonly used for providing pain relief is ablation in which nerves and/or tissue is removed and/or destroyed. Two approaches to destroying tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which leads to coagulation necrosis. Because ion agitation, and thus tissue heating, is greatest in areas of highest current density (e.g., closest to the active electrode tip), necrosis is limited to a relatively small volume of tissue surrounding the RF electrode.

A form of cold ablation is cryoablation. During cryoablation, tissue is frozen or rapid freeze/thaw cycles are inflicted upon the tissue. There are many advantages to using cryoablation instead of radiofrequency ablation. For example, cryoablation is safer especially near critical vasculature and there is less risk of post-procedure neuritis or neuromas following neuroablation for the treatment of pain. Cryoablation allows treatment mapping pre and post procedure where areas of tissue can be mapped by limited, reversible and/or freezing. Cryoablation can be monitored and visualized on ultrasonography, CT and MRI. Moreover, because nerve cooling is anesthetic, cryoablation is a less painful procedure than thermal ablation techniques.

The current procedures and techniques using cryoablation used destroy tissue due to rupturing of cells and/or cell organelles within the tissue. Deep tissue freezing is affected by insertion of a tip of a cryosurgical device into the tissue, either transperineally, endoscopically or laproscopically, and a formation of, what is known in the art as, an ice ball around the tip. During freezing, ice formation within the extracellular space creates an osmotic gradient, resulting in cellular dehydration. Ice crystals then form within the cells causing cell membranes to rupture resulting in cell death.

In addition, when the adjacent tissues are present at opposite borders with respect to the freeze treated tissue and since the growth of the ice ball is in a substantially similar rate in all directions toward its periphery, if otherwise, the ice ball reaches one of the borders before it reaches the other border, and decision making must be made on whether to continue the process of freezing, risking damage to close healthy tissues, or to halt the process of freezing, thereby risking a non-complete destruction of the treated tissue.

Traditional cryoablation systems can provide removal capabilities of soft tissue via the application of single needles that form an ice ball centered on a tip, but may also cause a high level of collateral thermal damage. Further, these devices may suffer from an inability to control the area of necrosis in the tissue being treated. The low temperature generated by these systems causes freezing of the surrounding tissue, leading to increased pain and slower recovery of the remaining tissue. Further, the desire for a cryoablation device to provide for effective ablation of soft tissue may compromise the ability to provide consistent ablation without significant collateral damage.

Another problem with currently available cryoablation devices is that they attempt to destroy tissue by using a single probe, which generates a large ice ball that creates a larger area for ablation. As a result, there is an increase in the amount of surrounding tissue damage near the surgical site.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient destruction of nerve and/or soft tissue by ablating a larger surface area perpendicular to the device yet minimizing tissue damage proximal and distal to the device that can be used during a minimally invasive procedure and/or during an open surgical procedure. Further, there is a need for devices and methods that provide fine ablation capabilities of nerve and/or soft tissue. Devices and methods that do not cause a high level of collateral thermal damage and allow for the control of necrosis in the tissue being treated are also needed.

SUMMARY

Ablation devices and methods are provided that allow for monitoring and control of temperature, pressure and position of ablating probes to achieve a more precise destruction of the nerve tissue and other soft tissue in a minimally invasive procedure. The ablation devices and methods provided allow the tips of the device to be easily positioned in an optimal location to obtain improved ablation with minimal unwanted destruction to adjacent nerve and/or soft tissue.

In various embodiments, an ablation system or device is provided which comprises at least a probe configured to generate pressure and temperature for ablating unwanted soft tissue and/or nerve tissue and at least one monitoring device coupled to the probe for recording and regulating temperature, pressure and position of the probe. In other embodiments, the ablation device includes at least one imaging device coupled to the probe for identifying the area to be subjected to ablation.

In some aspects, the at least one monitoring device is configured to detect differences between motor neurons, sensory neurons and/or interneurons.

In other implementations, the ablation device can comprise a computer system coupled to the cryoprobe. The computer system can be programmed with software adapted to receive real time or retrospective time data from the at least one monitoring device and/or at least one imaging device in order to calculate optimal temperature, pressure, and position for the probe and for the area to be subjected to ablation.

In some embodiments, the ablation devices and methods provided allow destruction of nerves and other soft tissue via a minimally invasive procedure to alleviate pain. As before, the ablation devices comprise at least a probe having at least two prongs spaced apart and parallel to each other, the probe being coupled to a monitoring device and/or imaging device which devices control the temperature, pressure and position of the at least one probe. The at least two prongs each have an interior surface and an exterior surface and an internal passage disposed in the interior surface of the at least two prongs. A filament is disposed in the internal passage of the at least two prongs having an opening configured to release a pressurized material (e.g., gas or liquid) into the interior surface of the at least two prongs so as to cool the exterior surface of the at least two prongs to a temperature configured for ablating nerve and/or soft tissue.

In some embodiments, a cryoablation device comprises a probe having at least two prongs spaced apart and parallel to each other, the at least two prongs each having an interior surface and an exterior surface; an internal passage disposed in the interior surface of the at least two prongs; a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue at a facet joint.

In certain embodiments, methods for destroying nerves and other soft tissue via a minimally invasive procedure to alleviate pain are also provided. Destruction of the target nerve or soft tissue can eliminate and/or reduce pain symptoms. Specific clinical applications of the disclosed ablation instrument include destruction of nerves causing facet and discogenic back and leg pain, destruction of soft tissue causing stenosis pain symptoms, and many other orthopedic and oral maxillofacial pains.

In some embodiments, methods for ablating unwanted soft tissue and/or nerve tissue are provided including positioning at least an ablation probe coupled with at least one monitoring device and/or at least one imaging device at a location near an unwanted tissue and/or nerve tissue. The location of the unwanted soft tissue and/or nerve tissue can be identified from input of at least one monitoring device and/or at least one imaging device. Subsequently, the location of the unwanted soft tissue and/or nerve tissue is identified from input of at least one monitoring device and/or at least one imaging device; the at least one ablation probe is then applied to the confirmed location of the unwanted soft tissue and/or nerve tissue; and the ablation of the unwanted soft tissue and/or nerve tissue is confirmed. In other embodiments, the confirming steps comprise using non-ablative temperature and/or pressure based upon patient feedback and/or input from at least one monitoring device and/or at least one imaging device.

In other embodiments, a computer connected to the at least one ablation device and/or monitoring device and/or imaging device can also be provided, the computer programmed with software for accepting input from the at least one monitoring device and/or imaging device and configured to compute an optimal temperature, pressure and location for the ablation probe In some embodiments, methods of ablating a nerve and/or soft tissue include positioning a distal region of a probe of a cryoablation device adjacent a nerve or soft tissue to be ablated, the probe having at least two prongs spaced apart and parallel to each other, the at least two prongs each having an interior surface and an exterior surface, an internal passage disposed in the interior surface of the at least two prongs, a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
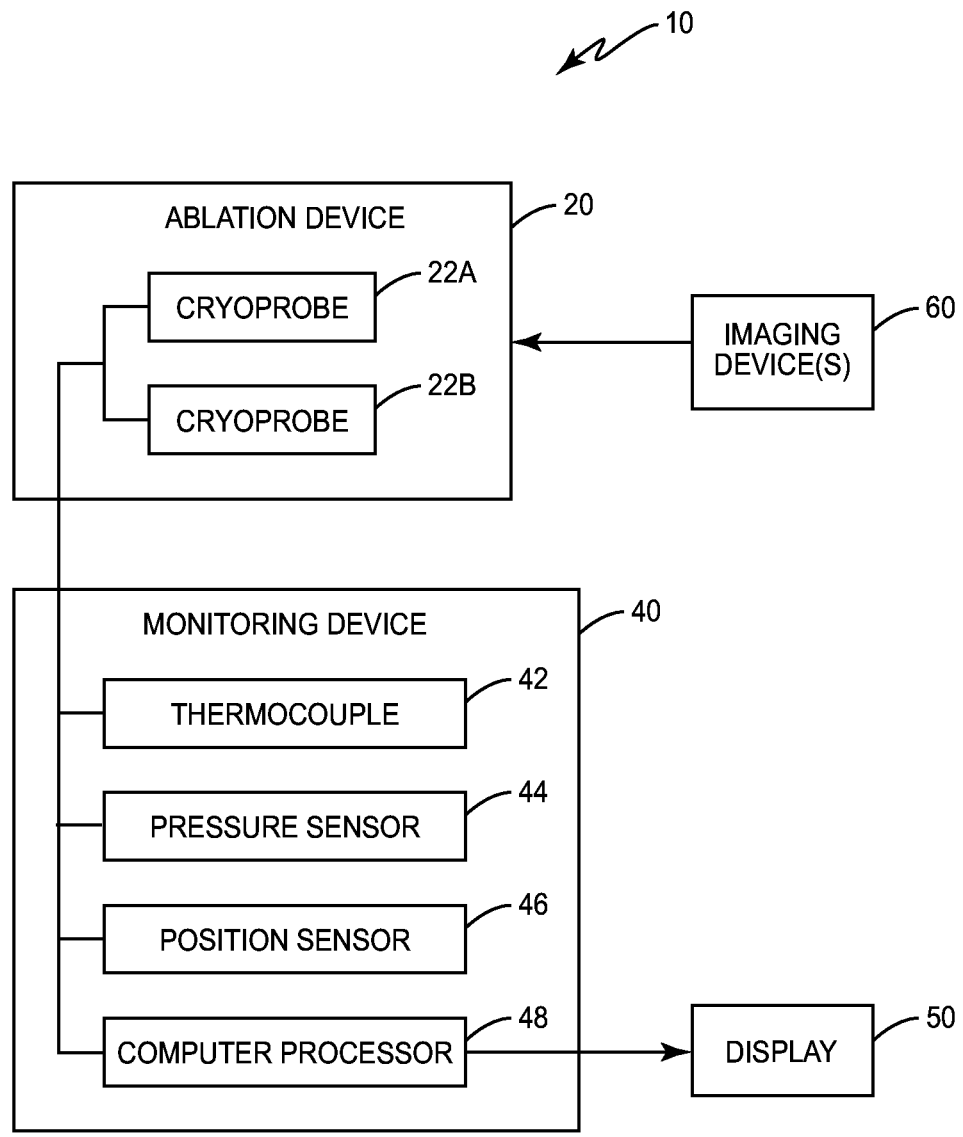
FIG. 1 is a block diagram of a cryoablation system according to one embodiment of this disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for efficient destruction and/or removing of a material or substance such as nerve and soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

Definitions

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Cryoablation

Cryoablation devices have been available to surgeons to treat many medical conditions, for example, in the treatment of tumors in lung, liver, kidney and other body organs. Cryoablation has also been used for treatment of tumors, cardiac arrhythmias, chronic and post-operative pain, bone fracture and soft tissue wounds.

Cold temperatures have been used to decrease inflammation and to relieve pain since the ancient Egyptians. Liquid air and carbon dioxide were used to treat skin lesions in the beginning of the twentieth century. In 1950, liquid nitrogen was introduced into clinical practice for the cryosurgical ablation of a variety of skin diseases and allowed for deeper tissue to be treated with cryoablation. In 1961, a liquid nitrogen probe was developed and was used to treat Parkinson's disease as well as inoperable brain tumors. From 1980-2000, systems emerged based on an advanced gas expansion method known as the Joule-Thomson Principle. This principle allows for temperature change of a gas or liquid when it is forced through a valve or porous plug while being kept insulated so that no heat is exchanged with the environment. The refrigerant could be stored at room temperature and the difficulties associated with supplying liquid nitrogen to the operating room disappeared. Three main refrigerants were utilized: nitric oxide, liquid nitrogen and argon. For over 20 years, rigid cryoprobes have existed for percutaneous use or in open invasive surgical procedures. For example, cryoprobes are used for freezing a range of lesions from prostate tissue to metastatic cancers in liver. Neuronal tissue has been frozen with such devices for the relief of pain.

Current cryoablation procedures and technique employ cryoprobes that utilize single needles that form an ice ball centered around a tip. The ice ball is essentially spherical or oval in shape and the area of complete nerve ablation is only approximately half of the ice ball diameter. Therefore, to ablate a particular area the ice ball needs to be approximately twice as large resulting in unnecessary tissue damage proximal and distal to the needle tip. As one travels up the probe toward the source of pressurized liquid or gas the temperature increases. Therefore, the probe of the present disclosure focuses the about −40° C. temperature at or near the tip for enhanced ablation.

The present disclosure provides an ablation device coupled to a monitoring device configured to record and regulate the pressure, temperature and/or position of the probe in order to ablate unwanted soft tissue and/or nerve tissue.

In some embodiments, the monitoring device can monitor not only temperature and pressure but also neuronal activity at the location of or in the vicinity of the probe. Functionally, neurons can be classified as afferent neurons, efferent neurons and interneurons. Afferent neurons bring information from tissues and organs into the central nervous system and are sometimes also called sensory neurons. Efferent neurons convey signals from the central nervous system to the effector cells and are sometimes called motor neurons. Interneurons connect neurons within specific regions of the central nervous system. In other embodiments, the monitoring device coupled to at least a cryoprobe can differentiate the activity of different neuronal populations, for example, motor versus sensory neuron activity or sensory A fibers versus sensory C fiber activity.

Useful monitoring devices comprise sensors that may receive and record data relating to temperature, light, density, impedance, and position of an ablation probe in the form of radiowaves, microwaves, spectroscopy, and the like. In different embodiments, sensors comprises a battery, an electrode, a recharger, a transmitter, a receiver, a transceiver, a sensor, a recorder, a capacitor, a transformer, a system control unit, a programmer, an address/positioning unit, a temperature sensor, a temperature adjuster, a thermogenerator, a thermoelectric generator, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator or a fuel cell.

In other embodiments the differential sensitivity can be due to the structure, size and/or composition of the tissue or neuronal cell type. In some instances, when combined with the appropriate monitoring sensors, the ablation device can be used to ablate all tissues within a certain area of the probe or only certain types of tissue or specific cell types within selected tissues.

In various aspects, the ablation device can also be coupled to an imaging modality such as ultrasound, CT, fluoroscopy or MRI, overhead 3D stereotactic system (via pre-procedure MRI and/or CT) allowing the user to visualize or otherwise identify the area covered by the unspecific or tissue/cell-specific ablation. For example, imaging devices useful in coupling with the ablation device described herein comprise without limitation Magnetic Resonance Imaging (MRI), functional Magnetic Resonance Imaging (fMRI), Magnetic Resonance Spectroscopy (MRS), diffusion MRI (DWI), diffusion tensor MRI (DTI), electroencephalography (EEG), magnetoencephalography (MEG), nuclear neuroimaging, positron emission tomography (PET), single photon emission computed tomography (SPECT), Ictal-Interictal SPECT Analysis by Statistical Parametric Mapping (ISAS), Computed Tomography (CT), x-ray, fluoroscopy, angiography, ultrasonography, transcranial magnetic stimulation (TMS), transcranial direct current stimulation (tDCS), transcranial electrical stimulation (TES), motor evoked potential (MEP), somatosensory evoked potential (SSEP), phase reversal of somatosensory evoked potential, evoked potential, electrocorticography (ECoG), direct cortical electrical stimulation (DCES), microelectrode recording (MER) or local field potential recording (LFP).

In some aspects, in order to control more accurately the temperature, pressure, flow rates of the coolant in the ablation device as well as the position of the ablation device, the monitoring device can be comprised of a thermocouple or a thermistor, a pressure sensor and a position sensor all in one control system or separate control systems. In some embodiments, the various sensors may be disposed on a component of the ablation device and/or can be positioned to contact the body tissue targeted for ablation.

In some embodiments, the device is coupled to software that enables the real time or retrospective review of the data coming from different navigation, monitoring and diagnostic tools used during the ablation procedure. For example, in various embodiments, the monitoring device can take many different forms. In some implementations, the monitoring device is a dedicated electrical circuit employing various sensors, logic elements, and actuators. In other implementations, the monitoring device is a computer-based system that includes a programmable element, such as a microcontroller or microprocessor, which can execute program instructions stored in a corresponding memory or memories. Such a computer-based system can take many forms, may include many input and output devices, and may be integrated with other system functions, such as the monitoring device, imaging device, a computer network, other devices that are typically employed during an ablation procedure. For example, a single computer-based system may include a processor that executes instructions to provide the function of the monitoring device; display imaging information associated with an ablation procedure (e.g., from an imaging device); display pressure, temperature, time information (e.g., elapsed time since a given phase of treatment was started) and probe position; and serve as an overall interface for the ablating device. In general, various types of monitoring devices are possible and contemplated, and any suitable monitoring device can be employed.

Cryoablation may be delivered to appropriate treatment sites inside a patient by a cryoablation probe. In various embodiments, a cryoablation probe generally includes a treatment component at its distal end with a cooling chamber inside, such as a metal tip or an expandable balloon. A cryogenic fluid may be provided by a source external to the patient at the proximal end of the cryablation probe and delivered distally through a lumen to the cooling chamber where it is released. Release of the cryogenic fluid into the chamber cools the chamber (e.g., through the Joule-Thomson effect), and correspondingly, the treatment component's outer surface, which is in contact with tissue that is to be ablated. Gas resulting from release of the cryogenic fluid may be exhausted proximally through an exhaust lumen to a reservoir or pump external to the patient. In some aspects, a cryoablation probe can include an elongate member and a treatment component disposed at a distal end of the elongate member. The elongate member can have lumens disposed therein to supply a cryogenic agent to an internal chamber of the treatment component and to channel exhaust from the internal chamber. The cryoablation probe can further include a monitoring device programmed to control the temperature, pressure and position of the probe, during a cryoablation procedure in which an outer surface of the treatment component is in contact with body tissue of a patient, a supply rate at which the cryogenic agent is supplied to the internal chamber and an exhaust rate at which exhaust is channeled from the internal chamber.

In certain embodiments, the probe can be in the range of 16-22 gauge with a bevel or hemispherical ending. In other embodiments, the probe includes a deployable balloon that can exert pressure on the surrounding tissue or increase surface area coverage of diffuse nerve fibers. In other embodiments, the probe includes channels for the circulation of a refrigerant. Examples of refrigerants include nitric oxide, carbon oxide, argon, liquid nitrogen, helium. In other embodiments, the probe contains a port for release of substance useful for navigation and/or monitoring. In some embodiments, the probe can comprise a dual needle configured for ablation that can simultaneously monitor the temperature and/or pressure within the body of the patient.

In yet other implementations, the probe can incorporate at least two or more parallel needles into a single device that is capable of ablating over a large surface area perpendicular to the needles. The needles operate simultaneously and are positioned over a specific distance apart from each other such that the zone of complete ablation merge or overlap with each other resulting in a larger continuous perpendicular ablation area than a single needle is capable of. The present disclosure forms smaller ice balls such that less adjacent tissue damage occurs.

As illustrated in FIG. 1, in some embodiments, a cryosurgical instrument or system 10 comprises an ablation device 20 including a plurality of cryoprobes 22a, 22b, etc., a monitoring device 40, an imaging device(s) 60 and a display unit 50. Each cryoprobe 22a, 22b, etc. can be needle shaped, in the range of 16 to about 22 gauge with a bevel or hemispherical ending and is cooled by a cooling agent, such as liquid nitrogen, nitrogen oxide gas or carbon dioxide gas, which is circulated through the cryoprobe. The operation of cryoprobes 22a, 22b, etc. is controlled by monitoring device 40 which is connected to ablation device 20. Monitoring device 40 comprises at least a temperature sensor (e.g., a thermocouple) 42, at least a pressure sensor 44, and at least a position sensor 46. In various embodiments, monitoring device 40 may include or be coupled to a computer processor 48 that executes instructions to provide the function of the monitoring device 40; a display unit 50 connected to the computer processor and provide imaging information associated with an ablation procedure (e.g., from an imaging device); display pressure, temperature, time information (e.g., elapsed time since a given phase of treatment was started) and probe position.

Figure 2:
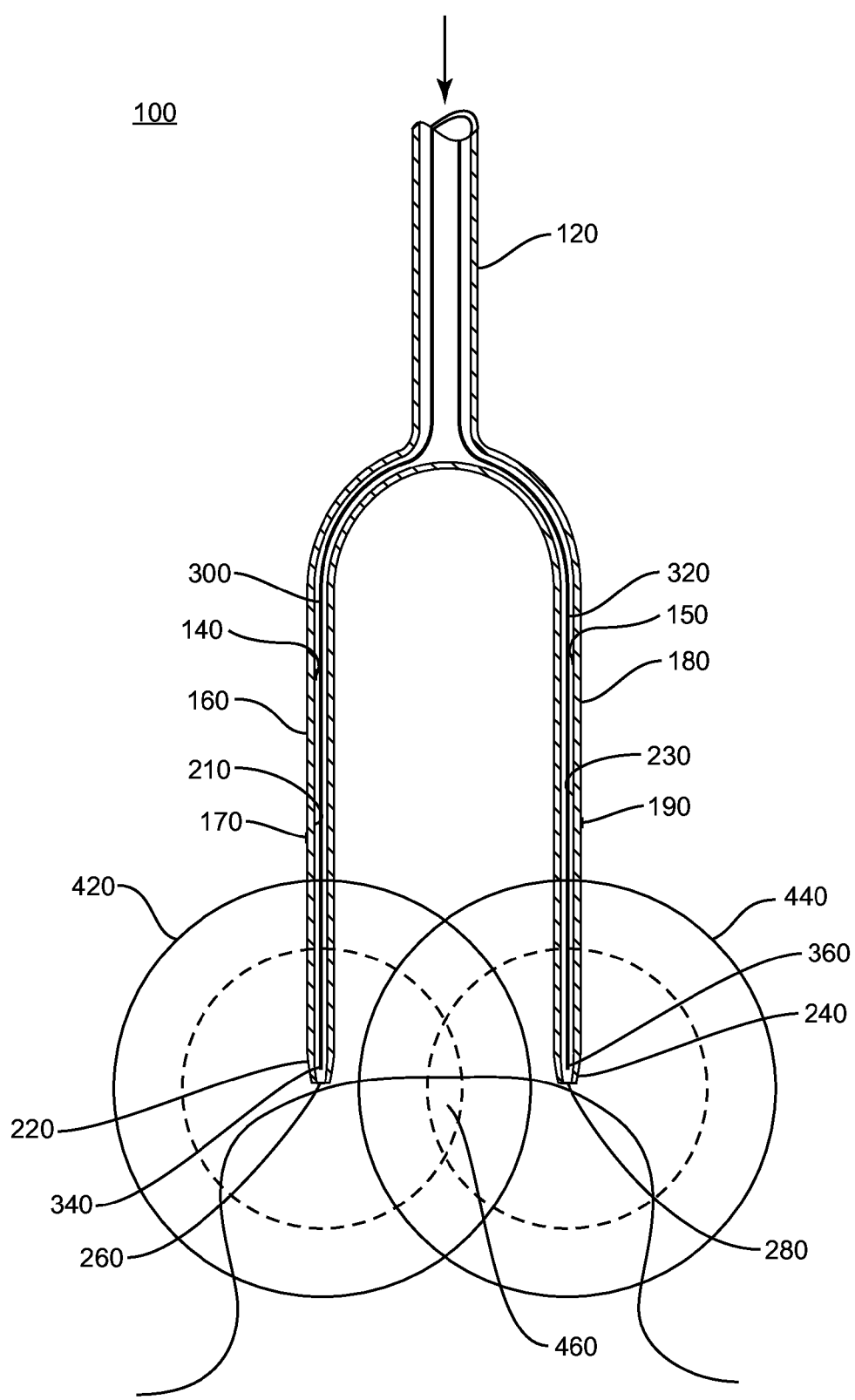
FIG. 2 illustrates a cross sectional front view of an ablation device in accordance with one embodiment of the present disclosure.

As illustrated in FIG. 2, in an embodiment, ablation device 100 comprises a probe 120. The dimensions of the probe, among other things, will depend on the site that needs ablation. For example, the width of the epidural space is only about 3-5 mm for the thoracic region and about 5-7 mm for the lumbar region. Thus, the probe, in various embodiments, can be designed for these specific areas.

Some examples of lengths of the probe, may include, but are not limited to, from about 50 to 150 mm in length, for example, about 65 mm for epidural pediatric use, about 85 mm for a standard adult and about 110 mm for an obese adult patient. The thickness of the probe will also depend on the site of that needs ablation. In various embodiments, the thickness includes, but is not limited to, from about 0.05 to about 1.655 cm. The probe may be the widest or smallest diameter or a diameter in between for insertion into a human or animal body. The widest diameter is typically about 14 gauge, while the smallest diameter is about 25 gauge. In various embodiments the probe can be about 16 to about 22 gauge.

Probe 120 includes at least two prongs, such as, for example, a first prong 160 and a second prong 180. Prongs 160, 180 are needles that are spaced apart and are parallel to each other. Prongs 160, 180 are spaced about at about a distance of 0.5 cm. In some embodiments, prongs 160, 180 are spaced apart at about 0.2 to about 0.4 cm. In some embodiments, prongs 160, 180 are spaced apart at about 0.6 to about 0.8 cm. Prongs 160, 180 each have an interior surface 140, 150 and an exterior surface 170, 190. Prongs 160, 180 each include an internal passage 210, 230 disposed in the interior surfaces 140, 150 of prongs 160, 180, respectively. In some embodiments, prongs 160, 180 can have one or more passages in each prong for pressurized material to be released into the prong as well as recirculation throughout the prong. Exterior surface 170 of prong 160 comprises a tip 220 and exterior surface 190 of prong 180 comprises a tip 240 positioned at a distal end of the probe. Tips 220, 240 are pointed to allow for easy pushing through tissues and include openings 260, 280 respectively.

In some embodiments, the tips of the prongs can be round or tapered. In various embodiments, the tips are smooth for insertion. In some embodiments, the probe 120 has a blunt tip such that the surgeon or health practitioner can eliminate any difficulty in positioning the probe tip in the optimal location to get an optimal and consistent clinical result. The use of probe 120 results in avoiding necrosis of adjacent tissue, which can lead to clinical adverse events that requires the tissue to undergo excessive repair itself after the procedure. In some embodiments, positioning of the tips 220, 240 allows ablation to be applied near the tips and avoids hemisphere spacing around the tips to avoid unwanted necrosis.

In some embodiments, a lubricant is provided to assist in the insertion of tips 220, 240 within the nerve and/or soft tissue. In some embodiments, the lubricant can be, without limitation, polyethylene glycol (PEG), hyaluronic acid, hyaluronan, lubricin, polyethylene glycol, and any combinations thereof.

In various embodiments, prongs 160, 180 are about 20 gauge. In some embodiments, prongs 160, 180 are about from 14 gauge to about 25 gauge. In some embodiments the prongs can be increasing and or decreasing in thickness throughout the prongs. In some embodiments, the prongs may be tapered and/or angled.

Prongs 160, 180 each comprise a filament 300, 320 disposed within internal passages 210, 230 of prongs 160, 180 respectively. Filaments 300, 320 are about 0.016 inches in diameter. In some embodiments, the filaments are about 0.010 to 0.015 or about 0.17 to about 0.25 inches in diameter. The filaments are conduits for cooling and expansion of the pressurized material that is released and passed into prongs 160, 180.

Filaments 300, 320 each include an opening 340, 360 configured to release a pressurized material into interior surfaces 140, 150 of the at least two prongs. The openings may be shaped as a regular or irregular polygon including arcuate, round, square, oblong, kidney shaped, crescent, or beveled shaped. The pressurized material is released into passages 210, 230 and enters into interior surfaces 140, 150, cooling and expanding within the interior surfaces via the filaments. The material is pressurized and in some embodiments, the pressure is from about 3,000 to about 6,000 pounds per square inch (PSI).

In some embodiments, the material is in the form of argon, liquid nitrogen, nitric oxide, helium, air, krypton, carbon dioxide, tetrafluoromethane or xenon. When a high pressure material such as argon is used, argon will expand within the interior and will liquefy so as to form a cryogenic pool at the tips, cooling the surfaces of the tips. The temperature of the material is coldest at the tips of probes 160, 180. In one embodiment, tips 220, 240 are made of a heat conducting material such as metal so as to enable the formation of the ice balls. The ice balls are spherical or oval in shape.

After a period of time, ice balls 420, 440 form when the exterior surfaces at the tips 220, 240 contact nerve and/or soft tissue and when the temperature at the tips decreases from about −40° C. to about −160° C. The temperature at the surface of the ice balls is 0° C. The temperature declines exponentially towards a cool center where it reaches about −170° C. The ice balls will be formed at about 2 to about 8 minutes after the material has been released into probe 120. The spheres create a zone of complete ablation (about −20° C.) typically located within each ice ball at approximately half way between the center of the ball and its outer surface. At least a portion of ice ball 420 comes into contact and/or overlaps with ice ball 440 and the overlapped area 460 along with the ice balls creates a larger continuous perpendicular ablation area than that of a single ice ball. Prongs 220, 240 create smaller ice balls, reducing the amount of damage caused to adjacent tissue.

The temperature for cryoablation of the device can be selected by the user and can vary as needed. For example, the temperature that can be selected can be from −180°, −170°, −160° −150° C., −140° C., −130° C., −120° C., −110° C., −100° C., −50° C., −40° C., −3° C., −2° C., −1° C., −5° C. or to about 0° C. or any temperature in between these numbers.

In some embodiments, a heated material can pass through the internal passages of the prongs to heat the pressurized material thereby increasing temperature.

The sizes of the tips of the prongs determine the sizes of the ice balls formed. In some embodiments, the diameter of the tips is about 0.5 to about 2 mm for smaller ice balls and from about 3 to about 6 mm for larger ice balls.

Figure 3:
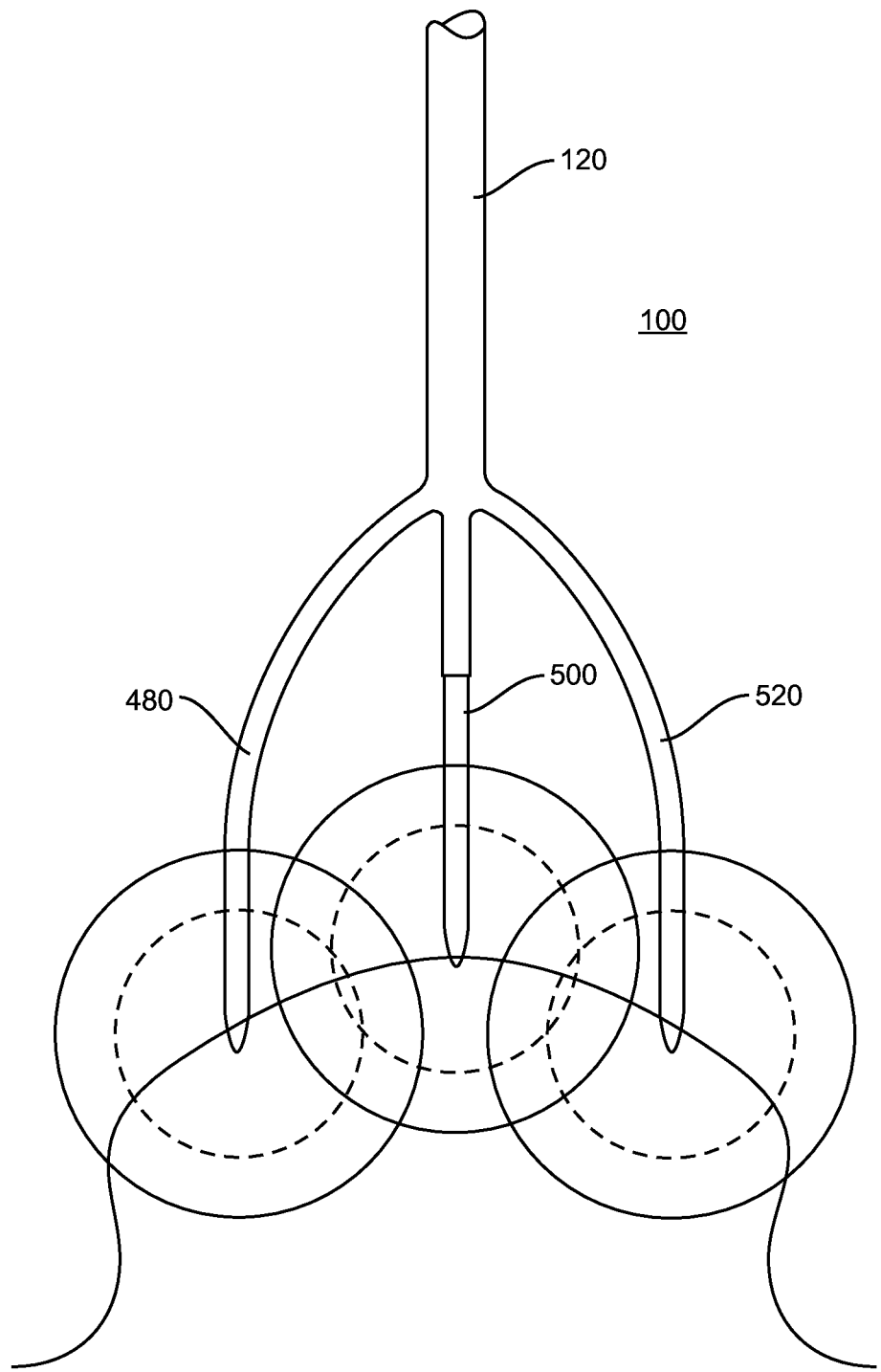
FIG. 3 illustrates a front view an ablation device in accordance with one embodiment of the present disclosure.

In one embodiment, as illustrated in FIG. 3, probe 120 comprises a plurality of prongs, such as, for example, a first prong 480, a second prong 500 and a third prong 520. Prongs 480, 500 and 520 comprise tips that form an arcuate configuration to match a particular geometry to be ablated. For example, in some embodiments, prongs 480 and 520 are longer than prong 500, such that when positioned with a facet of a vertebra, the facet geometry is matched with the tips of prongs 480, 500 and 520 and the prongs are in closer proximity to the overlying nerve fibers that require smaller ice balls for nerve ablation. In various embodiments, the prongs are configured to match other anatomical tissue shapes to treat other painful conditions. In certain embodiments, each prong may be introduced at a specific depth to locally provide treatment to a portion of the surgical site while avoiding damage to other areas that are not intended to be ablated.

In various embodiments, prong 500 comprises a telescopic configuration. Prong 500 can be manually or electronically movable so as to place prong 500 into a particular position within a surgical site. In certain embodiments, all or some of the prongs comprise a telescopic configuration. In some embodiments, prong 500 is a navigational tool used to guide probe 120 into a surgical site.

In some embodiments, the prongs each comprise indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the nerve and/or tissue.

In certain embodiments, probe 120 may include switches for manually controlling the operation of probe 120 by a medical practitioner. The switches can provide functions such as on/off, cooling, and predetermined cycles of heating and cooling by selectively and controllably communicating probe 120 with an external material container.

In some embodiments, different monitors of temperature, gas pressure and location on the probe 120 can be attached to probe 120. In some embodiments, thermal sensors may be used for measuring the temperature of the material and/or the tips of the prongs. In some embodiments, probe 120 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In some embodiments, probe 120 is attached to a pressure source that is configured to supply the pressurized material described above. In some embodiments, without limitation, the pressure source can be a pump, a cannula and or a catheter.

In various embodiments, at a proximal end, probe 120 can be operatively connected to a vacuum (not shown) for providing suction to ablated nerve and/or tissue. The vacuum may be used to transmit vacuum from a vacuum source (not shown) to a receiving aperture (not shown) connected to probe 120. Any suitable aspirator, cylindrical or otherwise, or other mechanism that creates vacuum upon the movement of an actuating member thereof, may be utilized as a vacuum source. The vacuum can be in communication with the tips of probe 120 for providing suction to remove ablated nerve and/or soft tissue.

With further reference to FIG. 2, not shown is an overall glass or other insulating layer covering most of the structure. In some embodiments, the coating or insulating layer can be glass or ceramic having a thickness from about 0.005 to about 0.5 mm thick or from about 0.01 to about 0.2 mm thick.

The glass type insulation is typically applied by a conventional process of dipping each relevant component prior to assembly in liquid (molten) glass and then annealing the glass. In some embodiments, the coating or insulation layer does not cover the entire probe. In some embodiments, the coating or insulation layer does cover the entire probe.

Suitable material for probe 120 can be for example, polyurethane, polyurea, polyether(amide), PEBA, thermoplastic elastomeric olefin, copolyester, and styrenic thermoplastic elastomer, steel, aluminum, stainless steel, titanium, nitinol, tungsten, molybdenum, metal alloys with high non-ferrous metal content and a low relative proportion of iron, carbon fiber, glass fiber, plastics, ceramics or a combination thereof.

In various embodiments, the probe may include radiographic markers to help indicate position on imaging procedures (e.g., CT scan, X-ray, fluoroscopy, PET scan, etc.). These may be disposed on or a portion of the probe or the prongs and include, but are not limited to, barium, calcium phosphate, and/or metal beads.

In some embodiments, probe 120 can also have blunt prong tips. As a result, the surgeon or health practitioner can eliminate any difficulty in positioning the probe tips in the optimal location to get an optimal and consistent clinical result. The use of probe 120 also results in avoiding necrosis of adjacent tissue, which can lead to clinical adverse events and requires these adjacent tissues to have to repair themselves. Positioning of the tips allows cryoablation to be applied near the tips and avoids hemisphere spacing around the tips to avoid unwanted necrosis.

In some embodiments, the tips of the prongs can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tips of the prongs and can be closed when probe 120 is inactive as probe 120 is inserted towards the desired location. Once the nerve or soft tissue to ablate is reached, grooves open, the material becomes activated to ablate the nerve or tissue protruding into each groove as probe 120 is manually pushed into it.

In certain embodiments, probe 120 can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the filaments in the prongs and can run parallel to the filaments such that the device can ablate and deliver a therapeutic material or barrier (e.g., polymer, cement, gel, etc.) to the area after ablating it.

Methods for Ablation

The present disclosure also provides methods of applying either pressure or low temperature or both together with positioning of at least one cryoprobe for the purpose of ablating unwanted soft tissue and/or nerve tissue. The method includes (i) navigation toward the targeted site using an imaging and/or monitoring modality, (ii) confirmation of the target using, for example, a diagnostic tool. In other embodiments, the target confirmation can be accomplished by using non-ablative low temperature and/or pressure based upon either patient feedback and/or a monitoring device. The first two steps are followed by (iii) ablation of the target tissue utilizing low temperature and/or pressure and (iv) confirmation of successful ablation using non-ablative low temperature and/or pressure based upon patient feedback and/or a monitoring device and/or visualization by imaging technique. The foregoing process can be repeated until all target tissues have been ablated. This method may be used to ablate the activities of neurons that are responsible in whole or in part for painful indications affecting bone, soft tissue, joint or cavity. In an alternative embodiment, the method could involve the use of two separate probes simultaneously to better target and ensure more effective nerve ablation.

In other embodiments, the present disclosure also provides methods for destroying or removing nerve and/or soft tissue. The methods comprise positioning a distal region of the cryoablation device 100 adjacent a nerve or soft tissue to be ablated, the probe having at least two prongs spaced apart and parallel to each other, the at least two prongs each having an interior surface and an exterior surface, an internal passage disposed in the interior surface of the at least two prongs, a filament disposed in the internal passage of the at least two prongs, the filament having an opening configured to release a pressurized material into the interior surface of the at least two prongs so as to cool the exterior surface of the at least two prongs to a temperature configured for ablating nerve and/or soft tissue. The exterior surface comprises a tip for the at least two prongs; or the exterior surface contacts nerve and or soft tissue to form an ice ball configured for ablating the nerve and/or the soft tissue; wherein the ice balls form at about 2-8 minutes, wherein at least a portion of each of the ices balls overlap causing the nerve and/or soft tissue to be ablate, and wherein the temperature of the pressurized material decreases at or near the tip and wherein the pressurized material is cooled at the tip at approximately −40° C., −100° C. or cooler.

In other embodiments, the methods of the present disclosure further include delivering cement and/or a polymer through a small channel, for injection at the site of the nerve and/or soft tissue destruction to provide a physically barrier at the location of the nerve destruction to prevent temporary or permanent nerve regrowth, repair and return of the pain symptoms. The barrier material utilized can be any suitable material effective to prevent or at least substantially inhibit the migration of substances that regrow tissue. Illustratively, the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement. In various embodiments, the barrier materials can be injected inside remaining residual membrane structures left after cryoablation of nerve tissues.

In several embodiments, the methods disclosed herein include operatively coupling the probe to a source of navigational capability to allow easier pushing through the tissues. In various embodiments, the methods of ablation disclosed herein can include a pre-procedure step wherein the probe can be coupled to a CT or MRI machine so that the target nerve and/or soft tissue to be ablated can be identified and accurately located during the destruction procedure.

The methods for ablation described hereinabove allow complete destruction of the nerve avoiding the problems and partial effectiveness of current cryoablation and RF devices available in the art, and also allow for more complete destruction of soft tissue that is causing stenosis pain symptoms.

Specific clinical application of this instrument include destruction of nerves causing facet and discogenic back and leg pain, destruction of soft tissue causing stenosis pain symptoms, and many other orthopedic and oral maxillofacial pain. Many other painful conditions associated with arthroscopic, otolaryngological or spinal procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An ablation device for ablating unwanted one of nerve tissue and soft tissue at a surgical site within a patient, the ablation device comprising:
   a probe configured to generate pressure and temperature for ablating the unwanted one of the nerve tissue and the soft tissue at the surgical site within the patient, the probe comprising at least two prongs, each prong of the at least two prongs including at least an exterior surface and a distal tip, each prong of the at least two prongs being configured to control at least a temperature of each respective exterior surface to achieve an ablation temperature on each respective exterior surface, the ablation temperature being adapted to ablate the unwanted one of the nerve tissue and the soft tissue at the surgical site within the patient; and
   at least one monitoring device coupled to the probe for recording and regulating temperature, pressure and position of the probe;
   wherein the distal tips of at least two prongs are configured to define, in combination, a probe geometry substantially matching an anatomical tissue geometry of the unwanted one of the nerve tissue and the soft tissue at the surgical site within the patient.

2. An ablation device according to claim 1, further comprising at least one imaging device coupled to the probe for identifying the unwanted one of the nerve tissue and the soft tissue at the surgical site within the patient.

3. An ablation device according to claim 1, wherein the at least one monitoring device is configured to detect differences between motor neurons, sensory neurons and/or interneurons.

4. An ablation device according to claim 2, further comprising a computer system coupled to the probe, the computer system programmed with software adapted to receive real time or retrospective time data from one of the at least one monitoring device and at least one imaging device to calculate optimal temperature, pressure, and position for the probe and for the unwanted one of the nerve tissue and the soft tissue at the surgical site within the patient.

5. An ablation device according to claim 1, wherein the at least two prongs are spaced apart and substantially parallel to each other, each prong of the at least two prongs further comprising an interior surface; an internal passage disposed in the interior surface; and a filament disposed in the internal passage, the filament having an opening configured to release a pressurized material into each interior surface, the pressurized material adapted to control the temperature of each respective exterior surface of the at least two prongs to achieve the ablation temperature of the unwanted one of the nerve tissue and the soft tissue at the surgical site within the patient.

6. An ablation device according to claim 1, wherein the at least one monitoring device comprises at least one of a battery, an electrode, a recharger, a transmitter, a receiver, a transceiver, a sensor, a recorder, a capacitor, a transformer, a system control unit, a programmer, an address/positioning unit, a temperature sensor, a temperature adjuster, a thermogenerator, a thermoelectric generator, a pressure sensor, a pressure adjuster, a mechanical power generator, a photo/light generator, an ultraviolet light generator, an infrared generator, an optical stimulator, a laser, a radiofrequency generator, a magnetic field generator, a mechanical vibration generator, an ultrasonic wave generator, an electrical field generator, a radiation generator and a fuel cell.

7. An ablation device according to claim 2, wherein the at least one imaging device comprises at least one of an ultrasound device, an overhead 3D stereotactic system, a Magnetic Resonance Imaging (MRI) device, a functional Magnetic Resonance Imaging (fMRI) device, a Magnetic Resonance Spectroscopy (MRS) device, a diffusion MRI (DWI) device, a diffusion tensor MRI (DTI) device, an electroencephalography (EEG), magnetoencephalography (MEG) device, a nuclear neuroimaging device, a positron emission tomography (PET) device, a single photon emission computed tomography (SPECT) device, an Ictal-Interictal SPECT Analysis by Statistical Parametric Mapping (ISAS) device, a Computed Tomography (CT) device, an x-ray device, a fluoroscopy, an angiography device, an ultrasonography device, a transcranial magnetic stimulation (TMS) device, a transcranial direct current stimulation (tDCS) device, a transcranial electrical stimulation (TES) device, a motor evoked potential (MEP) device, a somatosensory evoked potential (SSEP) device, a phase reversal of somatosensory evoked potential device, an evoked potential device, an electrocorticography (ECoG) device, a direct cortical electrical stimulation (DCES) device, a microelectrode recording (MER) device, and a local field potential recording (LFP) device.

8. An ablation device according to claim 1, wherein at least one prong of the at least two prongs has a substantial shape of a needle from about 16 to about 22 gauge.

9. An ablation device according to claim 6, wherein at least one prong of the at least two prongs comprises one of a substantially beveled end and a substantially hemispherical end.

10. An ablation device according to claim 1, wherein the end of at least one prong of the at least two prongs comprises a deployable balloon configured to one of exert pressure on surrounding tissue and increase surface area coverage of diffuse nerve fibers at the surgical site in the patient.

11. An ablation device according to claim 5, wherein the pressurized material comprises at least one of argon, liquid nitrogen, nitric oxide, helium, air, krypton, carbon dioxide, tetrafluoromethane, xenon and a combination thereof.

12. An ablation device according to claim 1, wherein the respective exterior surface of at least one prong of the at least two prongs further comprises an opening, the opening being configured for release of a substance useful in monitoring or navigating the probe.

13. A method for ablating unwanted one of soft tissue and nerve tissue at a surgical site within a patient, the method comprising:
positioning at least one ablation probe, the at least one ablation probe coupled with one of at least one monitoring device and at least one imaging device, at a location near the unwanted one of the soft tissue and the nerve tissue, the ablation probe comprising at least two prongs, each prong of the at least two prongs comprising at least an exterior surface and a distal tip, and each prong of the at least two prongs being configured to control at least a temperature of each respective exterior surface to achieve an ablation temperature on each respective exterior surface, the ablation temperature being adapted to ablate the unwanted one of the soft tissue and the nerve tissue, the distal tips of the at least two prongs being configured to define, in combination, a probe geometry substantially matching an anatomical tissue geometry of the unwanted one of the soft tissue and the nerve tissue;
identifying a location of the unwanted one of the soft tissue and the nerve tissue from an input of the one of the at least one monitoring device and the at least one imaging device;
confirming the location of the unwanted one of the soft tissue and the nerve tissue from the input of the one of the at least one monitoring device and the at least one imaging device;
applying the at least one ablation probe to the confirmed location of the unwanted one of the soft tissue and the nerve tissue; and
confirming the ablation of the unwanted one of the soft tissue and the nerve tissue.

14. A method according to claim 13 further comprising providing a computer programmed with software for accepting the input from the at least one monitoring device and computing an optimal temperature, pressure and location for the ablation probe.

15. A method according to claim 13, wherein confirming the location of the unwanted one of the soft tissue and the nerve tissue and confirming the ablation of the unwanted one of the soft tissue and the nerve tissue comprises using one of non-ablative temperature and pressure based upon one of patient feedback and input from the one of the at least one monitoring device and the at least one imaging device.

16. A method according to claim 13, wherein the unwanted one of the soft tissue and the nerve tissue comprises neurons responsible for pain affecting at least one of bones, soft tissues, joints, and cavities.

17. A method of claim 13, wherein the at least two prongs are spaced apart and substantially parallel to each other, each prong of the at least two prongs each further comprising an interior surface; an internal passage disposed in the interior surface; and a filament disposed in the internal passage of the at least two prongs, the filament having an opening configured to release a pressurized material into the interior surface of the at least two prongs so as to control the temperature of each respective exterior surface to reach the ablation temperature of the unwanted one of the soft tissue and the nerve tissue at the surgical site within the patient.

18. A method according to claim 17, wherein the exterior surface of each prong of the at least two prongs contacts the unwanted one of the nerve tissue and the soft tissue to form an ice ball proximate each respective distal tip, the ice ball being configured for ablating the unwanted one of the nerve tissue and the soft tissue; wherein each ice ball forms in about 2-8 minutes, wherein at least a portion of each ice ball one of comes into contact with and overlaps the unwanted one of the nerve tissue and the soft tissue, thereby causing the unwanted one of the nerve tissue and the soft tissue to be ablated, wherein a temperature of the pressurized material decreases proximate the distal tip, and wherein the pressurized material is cooled proximate the distal tip to a temperature of about 0 degrees C. to about −160 degrees C. or cooler.

19. A method for ablating unwanted one of soft tissue and nerve tissue at a surgical site within a patient, the method comprising:
positioning an ablation probe, the ablation probe comprising at least two prongs coupled to each other, each prong of the at least two prongs comprising at least an exterior surface and a distal tip, each prong of the at least two prongs being configured to control at least a temperature of the respective exterior surface to achieve an ablation temperature the ablation temperature on each respective exterior surface being adapted to ablate the unwanted one of the nerve tissue and the soft tissue at the surgical site within the patient, the distal tips of the at least two prongs being configured to define, in combination, a probe geometry substantially matching an anatomical tissue geometry of the unwanted one of the soft tissue and the nerve tissue; and one of at least one monitoring device and at least one imaging device at a location proximate the unwanted one of the soft tissue and the nerve tissue;

identifying the location of the unwanted one of the soft tissue and the nerve tissue from an input of the one of the at least one monitoring device and the at least one imaging device;

confirming the location of the unwanted one of the soft tissue and the nerve tissue from the input of the one of the at least one monitoring device and the at least one imaging device;

applying the at least two prongs of the ablation probe to the confirmed location of the unwanted one of the soft tissue and the nerve tissue; and confirming the ablation of the unwanted one of the soft tissue and the nerve tissue.

20. A method of ablation of claim 18, wherein the at least two prongs of the ablation probe are applied simultaneously.

21. An ablation device according to claim 1, wherein the at distal tips of the least two prongs of the ablation probe are further configured, in combination, to define a plurality of anatomical tissue geometries within the patient.

22. An ablation device according to claim 1, wherein the at least two prongs of the ablation probe are configured to be inserted at a certain depth into the patient to ablate the unwanted one of the nerve tissue and the soft tissue at a portion of the surgical site within the patient.

23. An ablation device according to claim 1, wherein the at least two prongs of the ablation probe further comprise at least three prongs.

24. An ablation device according to claim 1, wherein the at least two prongs of the ablation probe are configured to cool the respective exterior surface to the ablation temperature of the unwanted one of the nerve tissue and the soft tissue at the surgical site within the patient.

25. An ablation device according to claim 1, wherein each prong of the at least two prongs of the ablation probe is further configured to form an ice ball at the respective distal tip.

* * * * *

UNITED STATES PATENT AND TRADEMARK OFFICE
CERTIFICATE OF CORRECTION

PATENT NO. : 9,198,707 B2
APPLICATION NO. : 13/835424
DATED : December 1, 2015
INVENTOR(S) : McKay et al.

It is certified that error appears in the above-identified patent and that said Letters Patent is hereby corrected as shown below:

On the Title Page, in Item (74), under "Attorney, Agent, or Firm", in Column 2, Line 1, delete "Sorell Lenna & Schmidt" and insert -- Sorell, Lenna & Schmidt, --, therefor.

On the Title Page, in Item (57), under "Abstract", in Column 2, Line 6, delete "tissue" and insert -- tissue. --, therefor.

In Column 4, Line 33, delete "disclosure:" and insert -- disclosure; --, therefor.

In Column 10, Line 26, delete "probes 160," and insert -- prongs 160, --, therefor.

In Column 10, Line 44, delete "Prongs 220," and insert -- Tips 220, --, therefor.

In Column 10, Line 51, delete "-3° C., -2° C., -1° C.," and insert -- -30° C., -20° C., -10° C., --, therefor.

In Column 18, Lines 5-6, in Claim 21, delete "the at distal tips of the least" and insert -- the distal tips of the at least --, therefor.

Signed and Sealed this
Third Day of May, 2016

Michelle K. Lee
*Director of the United States Patent and Trademark Office*